United States Patent [19]

Martin

[11] Patent Number: 4,722,805
[45] Date of Patent: Feb. 2, 1988

[54] MULTIFUNCTIONAL CORROSION INHIBITORS

[75] Inventor: Richard L. Martin, St. Louis, Mo.

[73] Assignee: Petrolite Corporation, St. Louis, Mich.

[21] Appl. No.: 771,525

[22] Filed: Aug. 30, 1985

Related U.S. Application Data

[63] Continuation-in-part of Ser. No. 648,917, Sep. 11, 1984, abandoned.

[51] Int. Cl.$^4$ ............................................. C23F 11/16
[52] U.S. Cl. ......................... 252/389.21; 252/8.555; 422/5; 422/12; 106/14.12
[58] Field of Search ............... 252/8.55 E, 389.21; 422/12, 5; 106/14.12

[56] References Cited

U.S. PATENT DOCUMENTS

| | | | |
|---|---|---|---|
| Re. 23,227 | 5/1950 | Blair, Jr. et al. | 252/390 X |
| 2,598,213 | 5/1952 | Blair, Jr. | 252/8.55 E |
| 3,116,249 | 12/1963 | Ratner et al. | 252/389.21 X |
| 3,516,922 | 6/1970 | Anzilotti | 252/8.55 E |
| 3,585,210 | 6/1971 | Redmore | 252/8.55 E X |
| 3,620,974 | 11/1971 | Stanford et al. | 252/8.55 E X |
| 3,736,110 | 5/1973 | Owston, Jr. et al. | 252/389.21 X |
| 3,740,336 | 6/1973 | Langenfeld et al. | 252/146 X |
| 3,846,071 | 11/1974 | Redmore | 252/8.55 E X |
| 3,909,447 | 9/1975 | Redmore et al. | 252/8.55 E X |
| 4,066,398 | 1/1978 | Hwa | 252/8.55 E X |
| 4,339,349 | 7/1982 | Martin et al. | 252/8.55 E X |
| 4,388,214 | 6/1983 | Oppenlaender et al. | 252/8.55 E X |

FOREIGN PATENT DOCUMENTS 3232921  3/1984  Fed. Rep. of Germany ................ 252/389.21

OTHER PUBLICATIONS

Grant, Julius (Editor), *Hackh's Chemical Dictionary*, (1972), McGraw-Hill, New York, "acyl", acylation, p. 16.

*Primary Examiner*—Matthew A. Thexton
*Attorney, Agent, or Firm*—Robert E. Wexler

[57] ABSTRACT

Corrosion inhibitors for ferrous metals are provided which afford protection from general corrosion and cracking-type corrosion, which inhibitors are reaction products of acylated polyamines and phosphate esters.

6 Claims, No Drawings

MULTIFUNCTIONAL CORROSION INHIBITORS

This application is a Continuation-in-Part application of Ser. No. 648,917, filed Sept. 11, 1984 and now abandoned.

BACKGROUND OF THE INVENTION

1. Field of the Invention

This invention relates to inhibition of corrosion of ferrous metals and, in particular, to inhibiton of corrosion of the cracking-type of ferrous metals in corrosive systems as contrasted with the more familiar corrosion wherein metal loss occurs and results in a thinning of the metal.

In particular, this invention relates to multifunctional corrosion inhibitors and the use of same to inhibit both general corrosion and cracking-type corrosion in corrosive systems.

Stress corrosion cracking has been defined as failure by cracking due to the combined action of corrosive material and stress, the stress being either external (applied) or internal (residual). Generally the cracking may be either intergranular or transgranular, depending upon the stressed metal and the corrosive material.

Not all metals susceptible to stress corrosion cracking are uniformly affected by any particular corrodant. For example, carbon steels are most susceptible to stress corrosion cracking in nitrate environments, copper alloys are most affected by ammonia, while austenitic stainless steels are most susceptible to stress corrosion cracking in chloride environments.

One of the troublesome areas of stress corrosion cracking has been that of austenitic stainless steels in contact with chloride environments. Some chloride solutions, such as solutions of alkaline or alkaline-earth chlorides, are so aggressive when heated that they will cause highly stressed austenitic stainless steels to crack in extremely short periods of time, which may be less than about 30 minutes. Extensively cold-worked or as-drawn parts are especially susceptible because of the high degree of internal stresses. However, even annealed parts will fail in relative short periods of time under extreme conditions and external stresses. On the other hand, completely unstressed austenitic stainless steel would be excellent for use in contact with chloride solutions because of its resistance to ordinary corrosion effects. The ferritic and martensitic stainless steels are also subject to stress corrosion cracking to a more limited extent.

Since the mechanism of stress corrosion cracking has not yet been established, the prior art has shown very little that can be done to prevent it. Some techniques have been developed, althought they are not highly successful or desirable.

Another type of stress corrosion cracking which occurs is due to the presence of hydrogen which is also called hydrogen embrittlement. This type of corrosion is due to hydrogen given off in the corrosion process and is generally aggravated by the presence of $H_2S$.

Hydrogen embrittlement of steel occurs when free hydrogen atoms adsorbed on the metal surface diffuse into the metal by intercrystalline or interstitial diffusion. Once in the steel the hydrogen may remain in atomic form or, upon reaching an interstitial void of larger than atomic dimensions, may combine to form internal pockets of hydrogen gas. Hydrogen is found to permeate preferentially in stressed regions and to enter the voids nearest the stressed regions.

The diffusion of hydrogen into the steel is accompanied by the formation of internal gas packets, initiation and promotion of cracks in high stress areas, and certain other phenomena which induce the condition characterized by delayed brittle failure of the steel and by reduced ability of the steel to support sustained loads.

Hydrogen embrittlement is induced in steel in a number of ways including, for example, acid pickling, cathodic cleaning, electroplating, electrochemical machining, heating in moist atmospheres, exposure to moisture under corrosive conditions as in gas and oil well drilling and production and exposure to hydrogen at elevated temperature and pressures.

Embrittlement of steels is known to occur in bodycentered cubic microstructures such as exist in tempered martensitic, bainite, lamellar pearlite and spheroidized structures, but fully austenitic steels are found to be quite resistant to such embrittlement. In general, higher strength steels, i.e., above about 200,000 p.s.i. ultimate tensile strength, are more susceptible to this type of failure although embrittlement has been found in steels having strength levels of 60,000 p.s.i. or lower. The composition of the steel is not an important factor in hydrogen embrittlement and no alloying element, either substitututional or interstitial, has been truly effective in retarding hydrogen induced delayed brittle failure.

In low tensile strength steels hydrogen absorbed in this way more frequently causes blisters rather than cracking failure.

Still another type of corrosion is corrosion fatigue which is a process of failure of alloys where alternating tensile stresses, rather than continuing tensile stresses as occurrs in stress corrosion cracking, are involved along with corrosion. There is a relationship between corrosion fatigue and stress corrosion cracking in many systems. In non-corrosion fatigue, failure starts with crack initiation at a stress riser followed by propagation due to mechanical metallurgical forces until the member fails. This propagation can occupy 90% of the specimen life. Corrosion hastens the process by causing stress rising pits to form on the surface and by causing either direct metal loss or metal weakening at the notch of the propagating crack by a stress corrosion cracking mechanism. Thus, a corrosion inhibitor effective against corrosion fatigue is both a good metal loss inhibitor as well as a good stress corrosion inhibitor.

In contrast to stress corrosion cracking, the conventional corrosion inhibitor inhibits corrosion due to metal loss by attack of the corrodant on the metal per se.

2. Prior Art

In general, amines are known to be general corrosion inhibitors. Also, amine/thiophosphate/thione reaction products are known to inhibit corrosion of the cracking-type and phosphate salts of amines are known as general corrosion inhibitors. Thus, U.S. Pat. No. 3,846,071 describes general corrosion inhibitors which are imidazoline salts, where the salt moiety is a phosphate ester of an oxyalkylated alcohol. The phosphorylating agent used to prepare the phosphate ester is orthophosphoric acid, polyphosphoric acid, acid halides of phosphoric acid and phosphorus pentoxide. Also, U.S. Pat. No. 3,959,177 describes cracking-type corrosion inhibitors which comprise a thione and a thiophosphate and which also may include an acylated amine.

SUMMARY OF THE INVENTION

In accordance with the present invention, it has now been found that inhibitors of both general corrosion and cracking-type corrosion are afforded by the reaction of a nitrogen base and a phosphate ester wherein the phosphate ester contains no oxyalkylate groups and the phosphorylating agent is phosphorus pentoxide.

DESCRIPTION OF PREFERRED EMBODIMENTS

The multifunctional corrosion inhibitors of the invention are nitrogen base/phosphate ester neutralization reaction products. Although the nitrogen bases described herein have good general corrosion inhibition properties, niether the nitrogen base nor the phosphate ester provide suitable cracking-type corrosion inhibition. Surprisingly, the product resulting from the neutralization interaction of the nitrogen base and phosphate ester provide excellent inhibition of both general and cracking-type corrosion.

Nitrogen Bases

A wide variety of these compounds are known to be corrosion inhibitors. The following are a few non-limiting examples: 1. Oxazolines (U.S. Pat. NO. 2,587,855) 2. Tetrahydropyrimidines (U.S. Pat. No. 2,640,029) 3. Imidazolines (U.S. Pat. No. Re. 23,227) 4. Pyrrolinediones (U.S. Pat. No. 2,466,530) 5. Amino amides (U.S. Pat. No. 2,550,582 and 2,598,213) 6. Quaternary amines (U.S. Pat. No. 2,659,693) 7. Monoamines, such as Rosin Amine (OIL GAS JOURNAL 46, No. 31, 91–6 (1946) Oxyalkylated Rosin Amine (U.S. Pat. No. 2,564,740) Rosin Amine+solubilizing agent (U.S. Pat. Nos. 2,564,757 and 2,564,753).

Amides of amino acids such as the sarcosines, for example, are suitable. Thus:

$$\underset{\text{RC}}{\overset{\text{O}}{\|}}-\underset{\text{N}}{\overset{\text{R}'}{|}}-\text{CH}_2\text{COOH}$$

R=fatty hydrocarbon group
R'=H, lower alkyl

The imidazolines are a member of the cyclic amidine family of compounds and are prepared in the manner described in U.S. Pat. No. Re. 23,227, U.S. Pat. No. 2,468,163, and elsewhere. They may be described, for example, as follows:

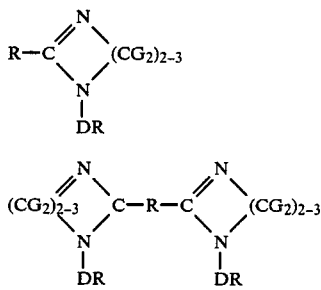

where

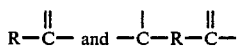

are residues derived from the carboxylic acid employed in preparing the compound, e.g. fatty acids or mixtures of fatty acids such as oleic and linoleic acids wherein R is, for example, a hydrocarbon radical, having, for example, up to about 30 carbon atoms, such a 1–30 carbon atoms, G is hydrogen or a hydrocarbon radical, for example, a lower alkyl, such as methyl - for example, where $CG_2$ is

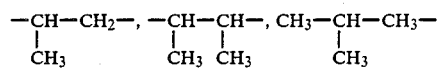

but preferably —$CH_2$—$Ch_2$— or —$CH_2$—$CH_2$—$CH_2$—, and R is the residue derived from the cyclic amidine-forming polyamine, for example where DR is —$C_nH_{2n}$—HR'—R',

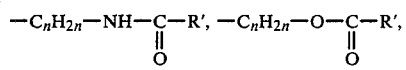

—$C_nH_{2n}$—O—R', —$C_nH_{2n}$—NR'—$C_nH_{2n}$—, NR'—R'—$C_nH_{2n}$—HR'—$C_nH_{2n}$—NR'—, $C_nH_{2n}$—HR'—R', or

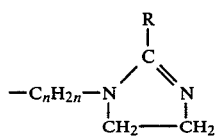

and wherein n is, for example, the numeral 1 to 6 and R' is hydrogen or an aliphatic or cycloaliphatic hydrocarbon radical.

In the simplest case, the group R' may be directly attached to the 1-nitrogen atom of the ring, as follows:

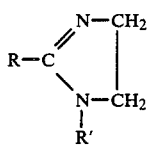

Particularly outstanding corrosion inhibitors result when the cyclic amidine contains basic nitrogen groups in addition to those inherently present in the imidazoline ring. In general, compounds of this type which are effective are those in which the basic nitrogen group is contained in the radical D in the above formula.

In this case the products may be represented by the formula

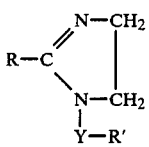

where R and R' are hydrogen or a hydrocarbon radical, and which at least one of the groups R and R' is an aliphatic or cycloaliphatic hydrocarbon group containing from 8 to 32 carbon atoms; and Y is a divalent organic radical containing amino groups. The group R' may be, and usually is, an amino nitrogen, substituent. Examples of organic radicals which Y—R' may represent are —C₂H₄—NR', —C₂H₄—NR'—C₂H₄—NR₂',
—C₃H₆—NR₂',

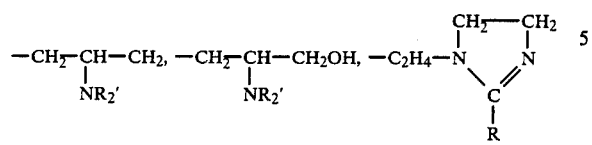

or —C₂H₄—NR—C₂H₄—NR'—C₂H₄—NR₂'
where R' and R have their previous significance.

Of this class of reagents, in which an amino group occurs as a portion of the 1-nitrogen substituent, those which are derived, at least theoretically, from the polyethylene polyamines appear to be particularly effective as corrosion inhibitors. These have the general formula:

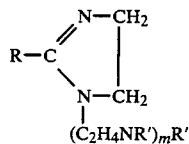

where R and R' have their previous meanings, and m is a smal number, usually less than 6. amides of these imidazolines are also effective.

In general, the preferred embodiments of film-forming corrosion inhibitors are of the type of cyclic amidines described above and acylated alkylene polyamines of the type described in U.S. Pat. No. 2,598,213 which are by reference incorporated in the present application.

The above cyclic amidines often contain amidoamines mixed in the reaction products. Thus, the term acylated polyamines includes both amidoamines and cyclic amidines.

Phosphate Esters

The phosphate esters used to prepare the inhibitors of the present invention are prepared by phosphorylating, with P₂O₅, an alcohol of the formula

R(OH)ₙ wherein R represents a hydrocarbon radical having from 1 to about 12 carbon atoms, preferably 6–8 carbon atoms, e.g. hexanol, heptanol, octanol and their isomers, e.g. isooctanol, and n represents an integer of from 1 to about 6. Accordingly, alcohols falling within the scope of the above formula include alkanols, e.g., methanol, decanol, dodecanol and the like; cycloalkanols, e.g. cyclohexanol; aryl alcohols, e.g., phenol and the like; polyols such as glycols and the like and similar materials.

The preparation of phosphate esters by the reaction of an alcohol, as described above, and P₂O₅ is well known to those skilled in the art. For purposes of the present invention, it has been found that phosphorylating agents other than P₂O₅ do not provide suitable phosphate esters. This may be, perhaps, because of the numerous side reaction products which may be afforded when using other phosphorylating agents such as orthophosphoric acid, polyphosphoric acid, phosphoric acid halides and the like. A number of known phosphorylation methods are described in "Structure and Mechanism in Organo-Phosphorus Chemistry", pp. 250–280 by R. F. Hudson, Academic Press, 1965 and "New Methods of Preparative Organic Chemistry", Vol. III, pp. 319–356, edited by W. Foerst, Adademic Press, 1964. Thus, in the present invention:

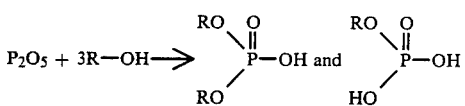

where R is defined above.

The following examples illustrate specific embodiments of the invention and the mode of operation thereof and are not to be considered as a limitation of the scope of the invention.

In the tests resulting in the data described in Tables I, II and III, the following inhibitor compounds and compositions are employed:

Inhibitor No. 1: Acylated Polyamine

RC(O)NH—(CH₂CH₂NH)ₓH and

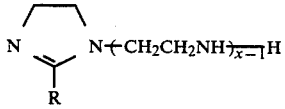

R = fatty acid residue
x = 3–10

As a tall oil fatty acid - dimeric acid salt

Inhibitor No. 2

Mixture of Inhibitor 1, a thiophosphate ester and an S-methylated-1,2-dithiole-3-thione as in U.S. Pat. No. 3,959,177

The thiophosphate structure is:

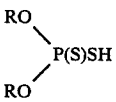

where
R = C₈₋₁₀H₁₇₋₂₁ —(OCH₂CH₂)₃—O
R = fatty acid residue
The 3-thione structure is:

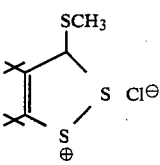

Inhibitor No. 3: Acylated Polyamine

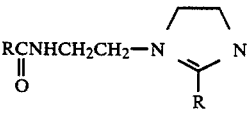

R = fatty acid residue

Inhibitor No. 4

Phosphate Ester reaction product of alcohol and $P_2O_5$

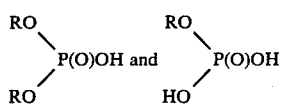

R = fatty acid residue

Inhibitor No. 5: Composition of the invention

Reaction product of Inhibitor 3 and Inhibitor 4

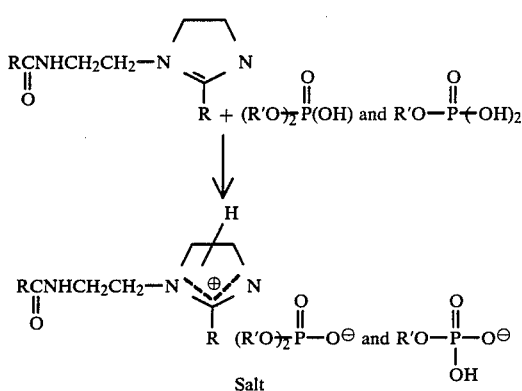

R = residue of mixture of fatty acids, e.g. oleic, linoleic
R' = alkyl of 5-12 carbon atoms

Inhibitor No. 6

Imidazoline salt where the salt moiety is a phosphate ester derived from an oxyalkylated alcohol using polyphosphoric acid as phosphorylating agent as in U.S. Pat. No. 3,846,071

Inhibitor No. 7: Thione component of Inhibitor 2

EXAMPLE 1

In this example, hydrogen permeation probe tests were used to simultaneously determine general corrosion and hydrogen penetration data (cracking-type corrosion) on a common steel surface.

Corrosion was measured by linear polarization resistance using the PAIR ® technique on the outer diameter of the probe, checked periodically with weight loss corrosion coupons. This probe is a hollow tube machined from hot rolled mild steel bar stock. Inside the probe, a potential of +0.250 V versus a copper reference electrode (about 0.000 V versus SCE in this environment) was held on the inner surface of the steel probe with a potentiostat; the filling solution was 1% NaOH and a central stainless steel tube was used as the counter electrode-cathode in this case. The entire probe assembly was inserted into controlled atmosphere, stirred, 2000 cc glass resin kettles, for these tests. This basic technique for measuring hydrogen has been used extensively, only the geometry was changed for presently reported tests. The current required to maintain the polarization, above a low base current, is proportional to hydrogen atom arrival and subsequent anodic oxidation at the inner diameter of the steel. Since the corrosion rate of steel even at slightly anodic potentials is quite low in 1% NaOH, the test is sensitive to very small quantities of hydrogen. After finish of each test, the probes were cleaned by a short dip in uninhibited 30% HCl, followed by rinsing in water and then acetone. Preliminary polarization inside the probe was established and maintained until the current dropped back to the base level of about 3 microamps total current. The outside of the probe was then abraded to a uniform surface with 240 grit silicon carbide paper, given a final wash, and inserted into the next test fluid at the same depth. The 3.5% NaCl test fluids were de-aerated before probe insertion, followed by saturation with $H_2S$ and inhibited using a concentration of 250 ppm inhibitor.

The results are summarized in Table 1:

TABLE 1

| INHIBITOR | % Protection Against General Corrosion | % Protection Against Hydrogen Entry |
|---|---|---|
| #1 | 96 | 88 |
| #2 | 97 | 94 |
| #3 | 94 | 80 |
| #4 | −73 | −225 |
| #5 | 96 | 98 |
| #6 | 97 | 76 |

The data show that the inhibitor of the present invention (#5) provides the same general corrosion protection but better cracking-type corrosion protection than the inhibitors of U.S. Pat. Nos. 3,846,071 and 3,959,177.

EXAMPLE 2

The tests described in Example 1 were continued using varying proportions of the components of Inhibitor 5 as compared with Inhibitors 6 and 7. The results of these tests, also in 3.5% NaCL solution at 250 ppm inhibitor, are summarized in Table II:

TABLE II

| Inhibitor | | | % Protection Against General Corrosion | % Protection Against Hydrogen Entry |
|---|---|---|---|---|
| % of #3 | % of #4 | % of other | | |
| 0 | 0 | 100 (Inhibitor #6) | 97 | 76 |
| 100 | 0 | 0 | 94 | 80 |
| 94 | 5 | 1 (Inhibitor #7) | 96 | 89 |
| 85 | 15 | 0 | 93 | 89 |
| 70 | 30 | 0 | 94 | 83 |
| 50 | 50 | 0 | 96 | 98 |
| 0 | 100 | 0 | −73 | −225 |

The data show that Inhibitor No. 5 is most effective at a 50/50 mixture of Inhibitor No. 3 and No. 4. Thus, a 50/50 mixture of No. 3 and No. 4 affords as good general corrosion protection as Inhibitors No. 6 and No. 7 but affords much greater hydrogen entry protection. The data further show that the 50/50 mixture, i.e. a 1/1 ratio of No. 3 to No. 4 is critical in obtaining high hydrogen entry protection. Thus, 70/30 and 85/15 mixture of No. 3 and No. 4 do not afford the hydrogen entry protection of the 50/50 mixture. The data also show that Inhibitors No. 3, 6, and 7, alone, afford no hydrogen entry protection and that Inhibitor No. 4, alone, affords neither general corrosion nor hydrogen entry protection.

EXAMPLE 3

In this example AISI 1040 steel U-bends of varying hardness were exposed to $H_2S$ saturated salt solutions to which corrosion inhibitors had been added. The cracking time was determined in accordance with NACE Test Method TM01-77. The results are summarized in Table III:

TABLE III

| INHIBITOR | Cracking Times for U-Bends | | | |
|---|---|---|---|---|
| | TEST A | TEST B | TEST C | TEST D |
| Blank | 2 hr | 15 hr | 16 min | 15⁻ hr |
| #1 | 14 hr | — | — | — |
| #2 | 156⁺ hr | — | — | — |
| #3 | — | — | 1.5 hr | — |
| #5 | — | 720⁺ hr | 50 hr. | 174⁺ hr |

Test A: Rockwell C40 in H₂S sat. 3.5% NaCl at room temp, 250 inhibitor
Test B: Rockwell C30 in H₂S sat. 5% NaCl, 0.5% HAc at room temp, 250 ppm inhibitor
Test C: Rockwell CHO in H₂S sat. 5% NaCl, 0.5% HAc at room temp, 250 ppm inhibitor
Test D: Rockwell C40 in 500 psi H₂S, 500 psi CO₂, 700 psi CH₄, 90% mixed brine, 10% kerosene, 54.4° C., in autoclave, 2000 ppm inhibitor
⁺indicates no failure in the indicated period
⁻indicates failure prior to the end of the indicated period
Test A and D approximate conditions in oil and gas wells, respectively.
Tests B and C are standard NACE cracking conditions.

Inhibitor concentrations in laboratory tests are typically higher than required under field corrosion conditions because of the short exposure periods and low volume to surface ratios found in laboratory tests. Typically, the inhibitors are effective at 5-500 ppm in the oilfield, often 10-50 ppm. In gas wells, the inhibitors are effective at 20-10,000 ppm, often 100-5000 ppm.

The mechanism of damage of the austenitic high alloy steels and the ferritic low carbon steels is felt by many investigators to differ from that of hardenable carbon and alloy steels. This latter kind of cracking and blistering is aggravated by the presence of hydrogen sulfide; many, but not all, investigators believe that the mechanism is the same in the presence of sulfide but just more severe.

It is generally felt that in this first type of cracking, e.g., stainless steel in chloride solutions or low carbon steel in nitrate solutions, cracking is due to a mechanism whereby corrosion takes place at an accelerated rate along some active path generated by a tensile stress-metal interaction. The second type of cracking system, high strength low alloy steels in brines or medium strength low alloy steels in H₂S laden fluids for example, is generally thought to only indirectly involve corrosion. As corrosion occurs on the metal surface, hydrogen ions are being discharged at the same time at this surface. These nascent hydrogen atoms have two alternative paths; they can combine to form molecules of hydrogen gas or they can dissolve into the metal lattice. It is then this penetrative hydrogen that causes blistering and cracking damage and sulfide can greatly increase the fraction of nascent hydrogen that dissolves into steel. The action of the tensile stress seems to be to concentrate this hydrogen at certain locations where damage then begins. One approach to minimizing cracking and blistering of ferrous alloys when hydrogen penetration is suspected to be causitive is to simply lower the corrosion rate thus reducing the amount of hydrogen available. The usefulness of this approach has been demonstrated in laboratory and field experiments. Laboratory and field experience has also demonstrated the benefits of further reduction, beyond that provided by conventional inhibitors, by use of the inhibitors of this invention.

As employed herein and in the claims "corrosion of the cracking type" means the following:
 1. stress (continuing tensile stress) cracking
 2. hydrogen embrittlement, blistering and stepwise cracking
 3. corrosion fatigue (alternating tensile stress).

It should be understood that the inhibitors of this invention may be used in admixture or in conjunction with other corrosion inhibitors and other chemical agents used in oil and gas wells such as emulsifiers, demulsifiers, scale inhibitors, polymer floods and the like.

While the illustrative embodiments of the invention have been described with particularity, it will be understood that various other modifications will be apparent to and can be readily made by those skilled in the art without departing form the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

I claim:

1. Composition comprising a 1/1 molar ratio of

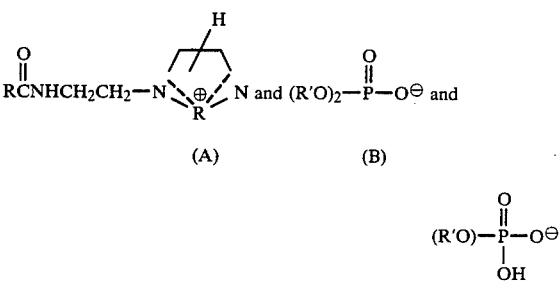

wherein R represents the residue of a fatty acid or mixture of fatty acids containing up to about 30 carbon atoms and R' represents an alkyl group containing from 1 to about 12 carbon atoms.

2. Composition of claim 1 wherein said mixture of fatty acids is a mixture of oleic and linoleic acids and said alkyl group contains 6-8 carbon atoms.

3. Composition of claim 2 wherein said alkyl group is isooctyl.

4. Method of inhibiting corrosion of ferrous metals in a corrosive system comprising adding to said system an effective corrosion inhibiting amount of the composition of claim 1.

5. Method of inhibiting corrosion of ferrous metals in a corrosive system comprising adding to said system an effective corrosion inhibiting amount of the composition of claim 2.

6. Method of inhibiting corrosion of ferrous metals in a corrosive system comprising adding to said system an effective corrosion inhibiting amount of the composition of claim 3.

* * * * *

UNITED STATES PATENT AND TRADEMARK OFFICE
CERTIFICATE OF CORRECTION

PATENT NO. : 4,722,805
DATED : February 2, 1988
INVENTOR(S) : Richard L. Martin

It is certified that error appears in the above—identified patent and that said Letters Patent is hereby corrected as shown below:

In Claim 1, delete Formula (A) and substitute therefor

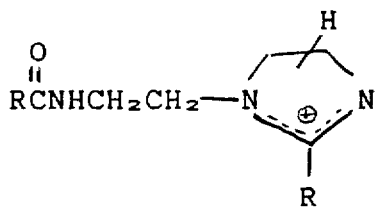

Signed and Sealed this

Fifth Day of July, 1988

*Attest:*

DONALD J. QUIGG

*Attesting Officer*   Commissioner of Patents and Trademarks